United States Patent [19]

Matsuoka et al.

[11] Patent Number: 5,277,818
[45] Date of Patent: Jan. 11, 1994

[54] ALBUMIN PREPARATION AND PROCESS FOR PREPARING THE SAME

[75] Inventors: Yasushi Matsuoka; Shinichiro Hase; Kazuo Takechi; Shinji Tomioka; Kazumasa Yokoyama, all of Osaka, Japan

[73] Assignee: The Green Cross Corporation, Osaka, Japan

[21] Appl. No.: 51,270

[22] Filed: Apr. 22, 1993

Related U.S. Application Data

[63] Continuation of Ser. No. 742,548, Aug. 8, 1991, abandoned, which is a continuation of Ser. No. 429,873, Oct. 31, 1989, abandoned.

[30] Foreign Application Priority Data

Oct. 31, 1988 [JP] Japan .................. 63-277082
Apr. 28, 1989 [JP] Japan .................. 1-111681

[51] Int. Cl.$^5$ .................................. B01D 15/08
[52] U.S. Cl. .................... 210/635; 210/656; 210/660; 530/364; 530/369; 530/416
[58] Field of Search ............ 210/635, 656, 660, 198.2; 530/364, 366, 368, 369, 413, 416, 417

[56] References Cited

U.S. PATENT DOCUMENTS

| 3,869,436 | 4/1975 | Falksveden | 530/364 |
| 3,992,367 | 11/1976 | Plan | 530/364 |
| 4,016,149 | 4/1977 | Travis | 210/635 |
| 4,043,997 | 8/1977 | Schroeder | 530/364 |
| 4,075,197 | 2/1978 | Schuck | 530/364 |
| 4,086,222 | 4/1978 | Lindquist | 210/635 |
| 4,093,612 | 6/1978 | Travis | 530/364 |
| 4,097,473 | 6/1978 | Lewis | 530/364 |
| 4,123,427 | 10/1978 | Daniel | 530/413 |
| 4,136,094 | 1/1979 | Condie | 530/364 |
| 4,210,722 | 7/1980 | Silver | 530/364 |
| 4,228,154 | 10/1980 | Fisher | 530/364 |
| 4,246,351 | 1/1981 | Miyake | 210/502.1 |
| 4,305,870 | 12/1981 | Liu | 530/364 |
| 4,534,972 | 8/1985 | Lembach | 530/364 |
| 4,546,161 | 10/1985 | Harvey | 530/364 |
| 4,576,928 | 3/1986 | Tani | 502/404 |
| 4,673,734 | 6/1987 | Tayot | 530/364 |
| 4,675,384 | 6/1987 | Dromard | 210/290 |
| 4,704,274 | 11/1987 | Sukuma | 530/413 |
| 4,720,385 | 1/1988 | Lembach | 530/380 |
| 4,754,019 | 6/1988 | Gion | 530/364 |
| 4,764,279 | 8/1988 | Tayot | 210/656 |

FOREIGN PATENT DOCUMENTS

| 0144714 | 6/1985 | European Pat. Off. | 210/198.2 |
| 2537123 | 3/1977 | Fed. Rep. of Germany | 210/198.2 |
| 213222 | 9/1984 | German Democratic Rep. | 530/364 |
| 88961 | 4/1987 | Japan | 530/364 |

OTHER PUBLICATIONS

Hawley The Condensed Chemical Dictionary, Van Nostrand Reinhold Company, N.Y., 1971, p. 483.
Chemical Abstracts, vol. 108, No. 25, No. 218559j.

*Primary Examiner*—Ernest G. Therkorn
*Attorney, Agent, or Firm*—Sughrue, Mion, Zinn Macpeak & Seas

[57] ABSTRACT

An albumin preparation having a polymer content of not more than 3% by weight based on the serum albumin content and an $\alpha_1$-AGP content of not more than a detectable limit based on the serum albumin content, which is prepared by removing a polymer-forming factor from an albumin aqueous solution by, for example, ion exchange separation or affinity chromatography, and subjecting the solution to a heat treatment.

3 Claims, 1 Drawing Sheet

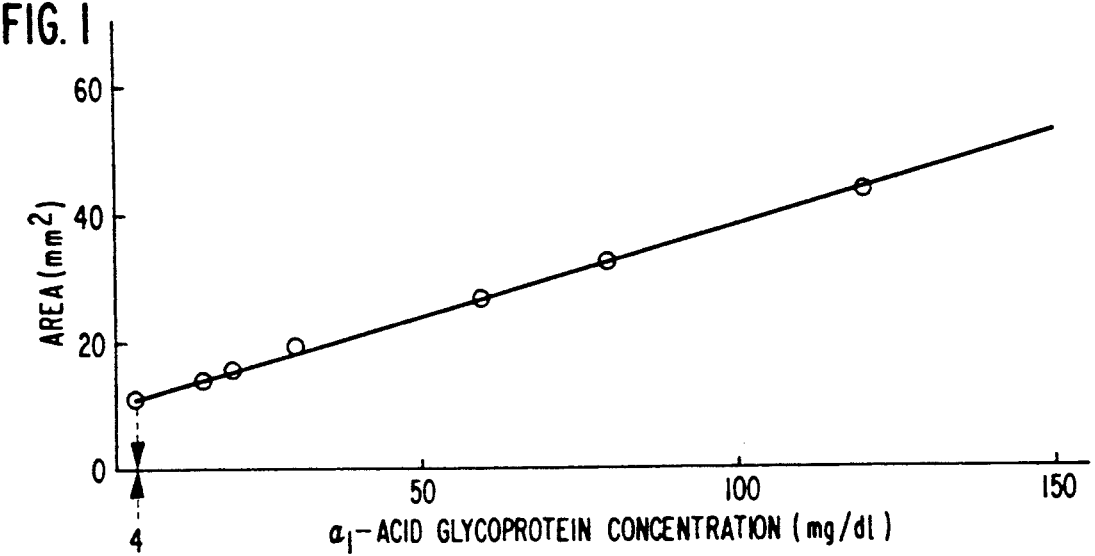
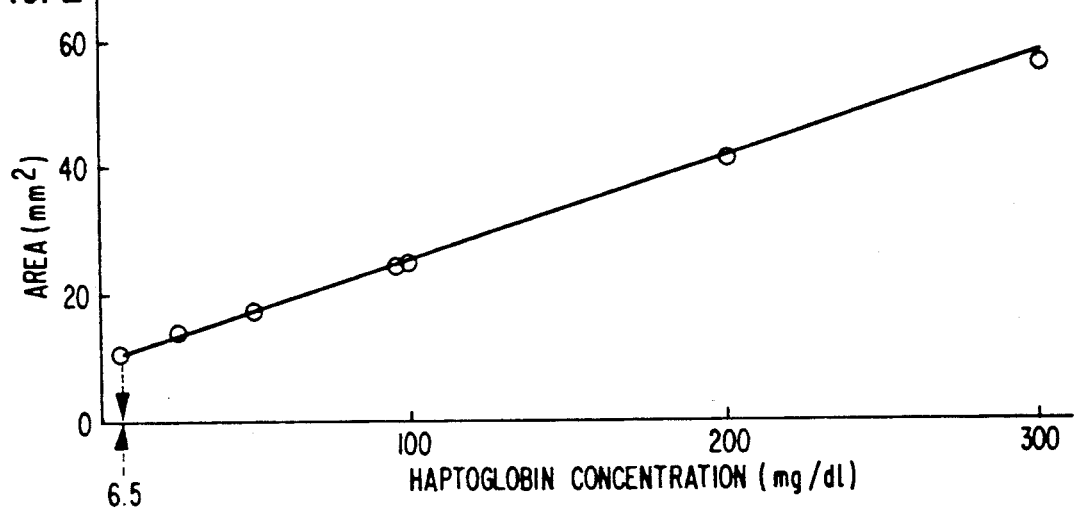
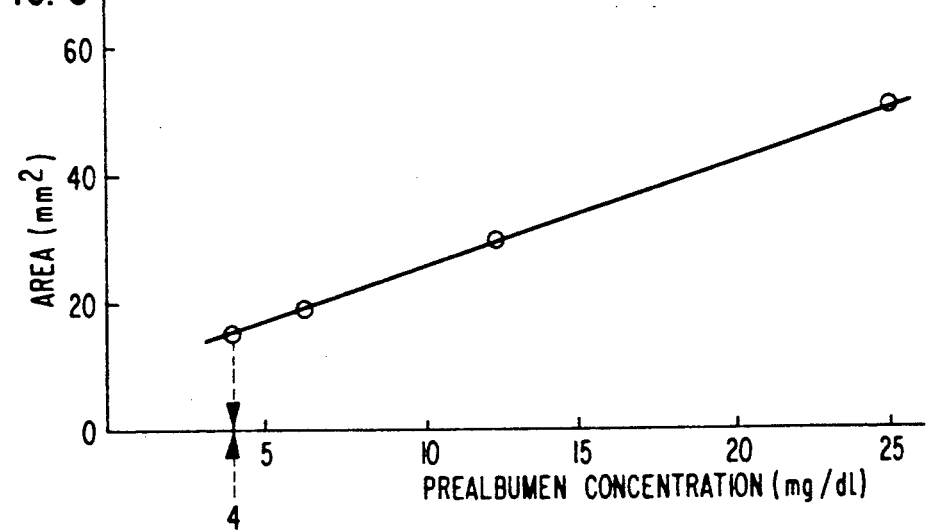

ALBUMIN PREPARATION AND PROCESS FOR PREPARING THE SAME

This is a continuation of application Ser. No. 07/742,548, filed Aug. 8, 1991, which is in turn a continuation of application Ser. No. 07/429,873, filed Oct. 31, 1989, both now abandoned.

FIELD OF THE INVENTION

This invention relates to an albumin preparation and a process for preparing the same. More particularly, it relates to a serum albumin preparation having a reduced content of agglomerates and a reduced content of contaminating proteins and to a process for preparing the same.

BACKGROUND OF THE INVENTION

Serum albumin is present in blood plasma in a proportion higher than any other plasma protein and functions to maintain an osmotic pressure or to carry nutrients, metabolites, etc. as a combination therewith in blood.

Preparations containing serum albumin are used in the treatment of hypoalbuminemia, hemorrhagic shock, etc. caused by albumin depletion or reduction of albumin biosynthesis. To deactivate viruses which may be incorporated into the albumin preparations, a heat treatment of an albumin-containing aqueous solution is generally carried out. It is known that commercially available albumin preparations obtained from the thus treated albumin aqueous solution contain agglomerates (hereinafter referred to as polymers as such agglomerates are commonly called) which have been formed during preparation. From the fact that no substantial polymers are found before the above-described heat treatment, it is believed that heat-labile proteins are partially denatured by the heat treatment to form polymers. Considering that the commercially available albumin preparations have been widely used with safety, these polymers are not regarded particularly harmful to human bodies. However, it is desired that the preparations contain no polymers because the polymers are heat denaturation products.

Further, albumin preparations also contain $\alpha_1$-acid glycoprotein (hereinafter referred to as $\alpha_1$-AGP), having an immunosuppressive activity, as an impurity. $\alpha_1$-AGP is a protein somewhat similar to albumin in physicochemical properties and, therefore, it is difficult to efficiently separate $\alpha_1$-AGP from albumin by commonly employed means, such as fractionation. Hence, there is a fear that usual albumin preparations contain residual $\alpha_1$-AGP having an immunosuppressive activity, and it is desired to remove $\alpha_1$-AGP from the preparations to the extent possible.

SUMMARY OF THE INVENTION

An object of this invention is to provide an albumin preparation having a reduced polymer content and a reduced $\alpha_1$-AGP content.

Another object of this invention is to provide a process for preparing the above-described albumin preparation.

As a result of extensive investigations, the inventors have found that formation of polymers is attributed to a polymer-forming factor (agglomerate-forming factor) present in albumin and that the polymer-forming factor is heat-labile contaminating proteins mainly comprising haptoglobin. It has also been found that an albumin preparation having reduced content of not only polymers but also of $\alpha_1$-AGP can be obtained, even if a heat treatment is carried out, by removing the polymer-forming factor from albumin. The present invention has been completed based on these findings.

That is, the present invention relates to an albumin preparation having a polymer content of not more than 3% by weight based on the serum albumin content and an $\alpha_1$-AGP content of not more than a detectable limit based on the serum albumin content, preferably not more that 4 mg/dl based on the albumin preparation.

The present invention also relates to a process for preparing an albumin preparation, which comprises subjecting a serum albumin aqueous solution to a step for removing a polymer-forming factor present in the solution and subjecting the solution to a heat treatment.

Removal of the polymer-forming factor is preferably achieved by at least one of ion exchange separation using an anion exchanger and affinity chromatography.

BRIEF DESCRIPTION OF THE DRAWINGS

FIGS. 1, 2, and 3 each shows a standard curve obtained by primary immunodiffusion against $\alpha_1$-acid glycoprotein, haptoglobin, and prealbumin, respectively.

DETAILED DESCRIPTION OF THE INVENTION

Albumin, which is the main ingredient of the preparation according to the present invention and also a starting material to be used in the process according to the present invention, is not particularly limited in its origin and includes albumin obtained from mammals, e.g., humans, cattle, rabbits, etc., with human-origin albumin being preferred. The starting material for preparing albumin includes the Fraction V obtained by Cohn's cold alcohol fractionation.

The albumin preparation of the present invention can be obtained by subjecting an albumin-containing aqueous solution to a step of removing a polymer-forming factor present in the solution and then subjecting the solution to a heat treatment. The albumin-containing aqueous solution is usually adjusted to have an albumin content of from 0.1 to 30% (weight/volume, hereinafter the same unless otherwise specified), preferably from about 1 to 10%.

Once it is known that the polymer-forming factor (e.g., haptoglobin) and $\alpha$hd 1-AGP which have an isoelectric point lower than that of albumin, various technique capable of removing these proteins from the albumin-containing aqueous solution can be used. Examples of suitable techniques include ion exchange separation using an anion exchanger and affinity chromatography. Haptoglobin, the main component of the polymer-forming factor, is hardly separated from albumin by fractionation because of its relative similarity to albumin in physicochemical properties.

In the case of using an anion exchanger, any insoluble carrier, e.g., dextran (Sephadex ®, etc.) agarose (Sepharose ®, etc.) cellulose (Cellulofine ®, etc.), polyacrylamide, vinylpolymer (Toyopearl ®, etc.) having an anion exchange group (e.g., dietylaminoethyl (DEAE) group, quarternarized amino ethyl group (QAE)) which is commonly employed in the art can be used. Specific examples of commercially available anion exchangers are DEAE-Sephadex ®, QAE-Sephadex ®, DEAE-Sepharose ® and Q-Sepharose ® (produced by Pharmacia); DEAE-Toyopearl ® and QAE-Toyopearl ® (produced by Tosoh); A200 Cellulofine ® (produced by Seikagaku Kogyo Co., Ltd.); and anion exchange resins. From the standpoint of polymer-forming factor removal efficiency, strong anion exchangers, e.g., Q-Sepharose ® and QAE-Toyopearl ®, are preferred.

Removal of the polymer-forming factor by using an anion exchanger can be effected by bringing the albumin-containing aqueous solution into contact with the anion exchanger. The amount of the anion exchanger to be used is selected appropriately depending on the polymer-forming factor content in the albumin aqueous solution, exchange capacity of the anion exchanger, and the like, usually ranging from 2 to 5 ml, particularly about 3 ml, per gram of albumin. The contact may be carried out either in a column system (ion exchange chromatography) or in a batch system, with the latter being preferred in view of removal efficiency.

Where a column system is employed, an albumin aqueous solution is adjusted so as to have a pH between about 4.8 and about 9.0, preferably between 4.9 and 5.5, more preferably 5.1, and a salt concentration of from 0.001 to 0.2M, preferably from 0.001 to 0.05M. The thus adjusted albumin aqueous solution is passed through a column packed with an anion exchanger equilibrated with an eluent, for example, 0.02M sodium acetate (pH=5.1). The column is then developed with the eluent, and the non-adsorbed fraction is collected. In order to prevent denaturation of albumin, these procedures are preferably carried out at low temperatures, usually 10° C. or lower, not less than 0° C.

Where a batch system is employed, an anion exchanger is added to an albumin aqueous solution having been adjusted in the same manner as described above, and the system is mixed at a temperature of 10° C. or less for about 30 minutes to 2 hours. The anion exchanger is then separated by appropriate means, such as centrifugation, and the supernatant liquor is recovered.

In the case of utilizing affinity chromatography, the carrier to be used is an insoluble carrier to which a substance exhibiting specific affinity for the polymer-forming factor, e.g., haptoglobin, is immobilized (hereinafter referred to as affinity carrier). Examples of suitable insoluble carriers are cellulose, agarose and dextran. The substance having specific affinity for the polymer-forming factor, e.g., haptoglobin, is selected according to the kind of the contaminating proteins. For example, an anti-haptoglobin antibody or hemoglobin is used for haptoglobin, and an anti-$\alpha_1$-AGP antibody is used for $\alpha_1$-AGP. These antibodies, e.g., an anti-haptoglobin antibody and an anti-$\alpha_1$-AGP antibody, can be prepared by known antibody production techniques. Bonding between the substance having a specific affinity and the insoluble carrier can be carried out in a usual manner. For example, agarose, e.g., Sepharose ®, activated by cyanogen bromide is swollen, and a substance having a specific affinity is coupled with the insoluble carrier in a basic buffer, followed by thoroughly washing with a buffer to obtain an affinity carrier.

Affinity chromatography is performed by contacting an albumin-containing aqueous solution containing the polymer-forming factor, e.g., haptoglobin, with the affinity carrier. For instance, the albumin-containing aqueous solution may be contacted with an affinity carrier to which a plurality of substances each having a specific affinity for the respective contaminating protein are immobilized; or it may be first contacted with an affinity carrier to which a substance having a specific affinity for haptoglobin is immobilized and then with an affinity carrier to which a substance having a specific affinity for $\alpha_1$-AGP is immobilized, if desired, followed by contact with other affinity carriers having specific affinities for other contaminating proteins.

The amount of the affinity carrier to be used ranges from 2 to 5 ml, usually about 4 ml, per gram of albumin, though depending on the content of the polymer-forming factor, e.g., haptoglobin, in the albumin-containing aqueous solution and adsorption capacity of the affinity carrier. From the viewpoint of efficiency in removal of the polymer-forming factor, it is preferable to carry out affinity chromatography in a column. For example, the albumin-containing aqueous solution is adjusted to a pH of from about 4.0 to 9.0, preferably from 5.0 to 8.0, more preferably 6.8, and passed through a column packed with the above-described affinity carrier having been equilibrated with a solvent used for dissolving albumin. If desired, the column is washed with the solvent for dissolving albumin to recover the non-adsorbed fraction. To inhibit denaturation of albumin, these procedures are preferably conducted at low temperatures (usually 10° C. or less).

The contaminating proteins can thus be removed to obtain an albumin-containing aqueous solution having its polymer-forming factor content reduced.

The albumin-containing aqueous solution having the thus reduced content of the polymer-forming factor is adjusted to have an appropriate concentration and formulated into any desired dose form, for example, charged into vials, followed by a heat treatment for deactivation of viruses. The heat treatment is generally given to an aqueous solution having an albumin concentration of from about 5 to 30% (w/v), usually about 5% (w/v) or from about 20 to 25% (w/v). The heat treatment is carried out under temperature and time conditions selected so as to sufficiently deactivate viruses, for example, at 50° to 70° C., preferably about 60° C., for 5 to 20 hours, preferably about 10 hours. If desired, a stabilizer for albumin, e.g., sodium N-acetyltryptophan and sodium caprylate, may be added either alone or as a mixture thereof to the albumin-containing aqueous solution to be heat-treated. The albumin stabilizer is added in an amount of from about 20 to 60 mg, preferably about 40 mg, per gram of albumin.

The thus obtained albumin preparation contains not more than 3% by weight of polymers based on albumin and contains not more than a detectable limit of $\alpha_1$-AGP based on albumin.

The albumin preparation according to the present invention can be used at the same dose in the same manner as for the conventional albumin preparations.

The albumin preparations of the present invention have the contaminating viruses deactivated by a heat treatment and the content of polymers and $\alpha_1$-AGP markedly reduced and are, therefore, excellent in safety, stability and the like.

According to the process of the present invention, viruses which may be incorporated into the preparations can be deactivated by a heat treatment, and since heat-labile contaminating proteins which form polymers on heat treating (polymer-forming factor), e.g., haptoglobin, have been removed before the heat treatment, the resulting albumin preparations have reduced content of polymers and contaminating proteins.

The present invention is now illustrated in greater detail by way of the following Examples, but it should be understood that the present invention is not deemed to be limited thereto.

EXAMPLE 1

Fraction V of plasma obtained by Cohn's cold alcohol fractionation was dealcoholized with acetone to obtain an acetone-dried powder, which was then dissolved in water to prepare an aqueous solution having an albumin concentration of 10%. After adjusting the pH to 5.1 with 10% (v/v) acetic acid, the solution was passed through a column of DEAE-Sephadex ® equilibrated with 0.02M sodium acetate (pH 5.1) at 4° C. To the effluent were added 20 mM of sodium N-acetyltryptophan and 20 mM of sodium caprylate, and the solution was poured into a vial and heat-treated at 60° C. for 10 hours to obtain an albumin preparation.

The polymer content in the resulting preparation was determined by gel chromatography through 4 replicate runs and was found to be 3.0% or less (relative percent by weight based on the albumin content, hereinafter the same with respect to polymer content).

For comparison, an albumin preparation was prepared in the same manner as described above, except that the treatment with DEAE-Sephadex was not conducted. As a result, the polymer content of the resulting preparation was found to be 6.3% (an average of the results of four replicate runs).

Then, the substance adsorbed onto DEAE-Sephadex ® was eluted with 5M magnesium chloride solution at room temperature, and the eluate was analyzed by gel chromatography and cellulose acetate electrophoresis. As a result, the adsorbed substance was found to be proteins mainly comprising haptoglobin.

EXAMPLE 2

Cyanogen bromide-activated Sepharose ® 4B (5.8 g) was swollen with 1 mM hydrochloric acid for 15 minutes and washed with water and then with a basic buffer [containing 0.1M sodium hydrogencarbonate and 0.5M sodium chloride (pH=8.3)]. In 40 ml of the same basic buffer was dissolved 100 mg of human hemoglobin, and 20 ml of the above obtained swollen gel was added thereto, followed by stirring for 2 hours. Then, 15 ml of 1M glycine (pH=8.0) was added thereto, and the system was stirred at 4° C. for 12 hours, followed by filtration. The gel collected was thoroughly washed with the same basic buffer as used above and equilibrated with a phosphoric acid-buffered sodium chloride aqueous solution to prepare human hemoglobin-immobilized Sepharose.

Separately, the acetone-dried powder of the Fraction V as used in Example 1 was dissolved in water to prepare a 10% albumin aqueous solution, and the solution was adjusted to a pH of 6.8 with sodium carbonate and sodium hydroxide. The solution (200 ml) was passed through a column packed with 20 ml of the above prepared Sepharose gel at 4° C., and an effluent was collected in 20 ml fractions. Haptoglobin in each of fraction Nos. 2 to 8 was determined by primary immunodiffusion (Mancini test described in Mancini et al., *Immunochemistry*, Vol. 2, No. 3, pp. 295-254, 1985). Further, each fraction sample (5 ml) was concentrated to 2 ml by means of Centricut-50, and 280 μl of a stabilizer solution containing 36 mg of sodium N-acetyltryptophan and 24 mg of sodium caprylate per ml was added to the concentrate, followed by heating at 60° C. for 10 hours to obtain an albumin preparation. The polymer content in the preparation was determined by gel chromatography. The haptoglobin (Hp) concentration of the effluent and the polymer content of the albumin preparation obtained therefrom are shown in Table 1 below.

TABLE 1

| Fraction No. | Hp Concentration (mg/dl) | Polymer content (%) |
| --- | --- | --- |
| 2 | 0 | 0.94 |
| 3 | 41.8 | 0.82 |
| 4 | 267.4 | 2.70 |
| 5 | 377.1 | 2.87 |
| 6 | 367.9 | 3.12 |
| 7 | 366.9 | 3.13 |
| 8 | 392.6 | 3.01 |

As can be seen from the results of Table 1, the lower the haptoglobin concentration in the effluent, the lower the polymer content of the resulting preparation. Taking the results of Examples 1 and 2 into account, it was proved that the polymer content can be reduced by removing contaminating proteins having an isoelectric point lower than that of albumin (mainly comprising haptoglobin).

EXAMPLE 3

The Fraction V obtained by Cohn's cold alcohol fractionation (300 g; albumin content: 110.2 g) was dissolved in 1.2 of cold germ-free distilled water, followed by stirring for about 1 hour. After adjusting to a pH of 4.6 with a 10 v/v % acetic acid aqueous solution, the solution was filtered (pore size: 0.45 μm) at about −2° C. To the filtrate was further added 1.2 l of cold germ-free distilled water, and the solution was adjusted to a pH of 5.1 with 0.8M sodium hydrogencarbonate to prepare an albumin aqueous solution.

Separately, 350 ml of QAE-Toyopearl ® was packed in a column, thoroughly washed with 500 ml of 0.5M sodium chloride, and equilibrated with 0.02M sodium acetate (pH=5.1) to prepare an anion exchanger column. The above prepared albumin aqueous solution was passed through the column, and the column was washed with 1.2 l of 0.02M sodium acetate. The effluent and the washing were combined, adjusted to a pH of 6.2 with 1N sodium hydroxide, and subjected to concentration with a Pellicon cassette system to give a total amount of 330 ml (albumin concentration: about 28%) (hereinafter referred to as adjusted albumin solution).

To the adjusted albumin solution was added 39.6 ml of a stabilizer solution containing 5.55 g of sodium N-acetyltryptophan and 3.89 g of sodium caprylate per 100 ml, and the solution was adjusted to a pH of 6.85 with 0.1N sodium hydroxide, followed by sterilization by filtration. After adjusting the albumin concentration to 25%, a prescribed amount of the solution was poured into a vial and heat treated at 60° C. for 10 hours to obtain an albumin preparation.

The polymer content in the resulting preparation was found to be 1.99% by gel chromatography.

For comparison, an albumin preparation was obtained in the same manner as described above, except that the treatment with the QAE-Toyopearl column was not conducted. The polymer content after the heat treatment was found to be 6.49%, revealing that the polymer content of the albumin preparation according to the present invention is markedly lower than that of the comaprative preparation.

Further, the contents of contaminating proteins in the adjusted albumin solution and the albumin preparation of the present invention were determined by primary immunodiffusion method (Mancini test) using a gel for primary immunodiffusion prepared using anti-$\alpha_1$-AGP, anti-haptoglobin or anti-prealbumin as an antibody. The results obtained are shown in Table 2 below. The anti-$\alpha_1$-AGP serum, anti-haptoglobin serum, and anti-prealbumin serum used were prepared from immunized rabbits in a usual manner. A standard curve of precipitated ring area formed by the reaction between each of the anti-serum and the corresponding contaminating protein is shown in FIGS. 1 to 3.

As is shown in Table 2, the adjusted albumin solution and the albumin preparation according to the present invention have extremely reduced contents of contaminating proteins. As is obvious from FIGS. 1 to 3, the detectable limits of haptoglobin, $\alpha_1$-AGP, and prealbumin were 6.5 mg/dl, 4 mg/dl, and 4 mg/dl, respectively.

TABLE 2

| Contaminating Protein | Content | |
| --- | --- | --- |
| | Adjusted Albumin Solution | Albumin Preparation |
| Haptoblobin | below detectable limit | below detectable limit |
| $\alpha_1$-AGP | below detectable limit | below detectable limit |
| Prealbumin | below detectable limit | below detectable limit |

While the invention has been described in detail and with reference to specific embodiments thereof, it will be apparent to one skilled in the art that various changes and modifications can be made therein without departing from the spirit and scope thereof.

What is claimed is:

1. A process for preparing an albumin preparation, which comprises subjecting a serum albumin aqueous solution to ion exchange separation using an anion exchanger, wherein said anion exchange separation is carried out at a pH ranging from 5.1 to 5.5, for removing a polymer-forming factor present in the solution and then subjecting the solution to a heat treatment sufficient to inactivate virus.

2. A process as claimed in claim 1, wherein proteins having an isoelectric point lower than that of albumin are removed.

3. A process as claimed in claim 1, wherein said anion exchange separation is carried out at a pH 5.1.

* * * * *